US00PP35997P2

(12) United States Plant Patent
van Sambeek

(10) Patent No.: US PP35,997 P2
(45) Date of Patent: Jul. 9, 2024

(54) ***PHLOX* PLANT NAMED 'DOPHLOWOBLU'**

(50) Latin Name: *Phlox hybrida*
Varietal Denomination: DOPHLOWOBLU

(71) Applicant: DUMMEN GROUP B.V., De Lier (NL)

(72) Inventor: Ellen van Sambeek, Oegstgeest (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/382,504

(22) Filed: Oct. 21, 2023

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phlox* plant named 'Dophlowoblu', characterized by its upright to outwardly spreading and mounding plant habit; vigorous growth habit; freely flowering habit; relatively large bright violet-colored flowers; and good garden performance.

2 Drawing Sheets

Figure 1:
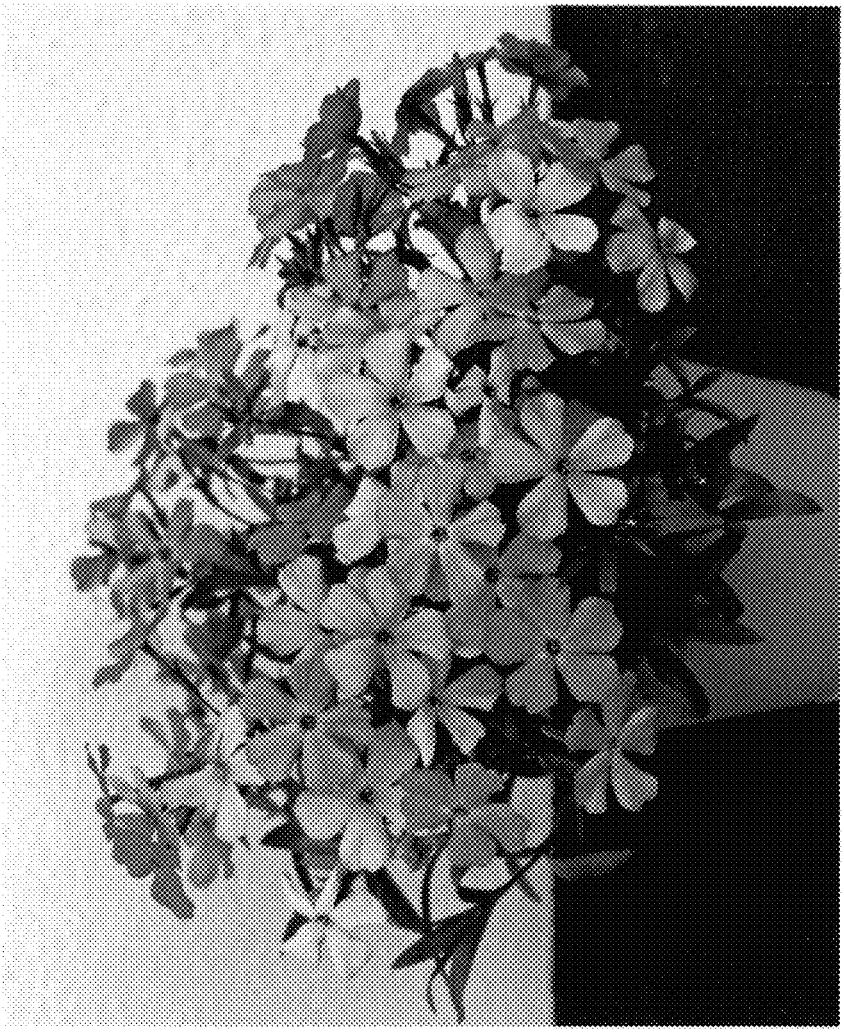

Botanical designation: *Phlox hybrida.*
Cultivar denomination: 'DOPHLOWOBLU'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 26, 2022, application number 2022/1998. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox hybrida* and hereinafter referred to by the name 'Dophlowoblu'.

The new *Phlox* plant is a product of a planned breeding program conducted by the Inventor in Aalsmeer, The Netherlands. The objective of the breeding program was to create new freely-flowering *Phlox* plants with large attractive flowers.

The new *Phlox* plant originated from a cross-pollination made by the Inventor in April, 2017 in Aalsmeer, The Netherlands, of a proprietary selection of *Phlox hybrida* identified as code number SB07-000252-016, not patented, as the female, or seed, parent with a proprietary selection of

*Phlox hybrida* identified as code number SB-0064, not patented, as the male, or pollen, parent. The new *Phlox* plant was discovered and selected by the Inventor as a single flowering plant from within the progeny of the stated cross-pollination in a controlled environment in Aalsmeer, The Netherlands in April, 2019.

Asexual reproduction of the new *Phlox* plant by vegetative cuttings in a controlled environment in Aalsmeer, The Netherlands since June, 2019 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophlowoblu'. These characteristics in combination distinguish 'Dophlowoblu' as a new and distinct *Phlox* plant:

1. Upright to outwardly spreading and mounding plant habit.
2. Vigorous growth habit.
3. Freely flowering habit.
4. Relatively large bright violet-colored flowers.
5. Good garden performance.

Plants of the new *Phlox* differ primarily from plants of the female parent selection in leaf shape as plants of the new *Phlox* have lanceolate-shaped leaves whereas plants of the female parent selection have subulate-shaped leaves.

Plants of the new *Phlox* differ primarily from plants of the male parent selection in flower placement as plants of the new *Phlox* have shorter peduncles and flowers are placed just above the foliar plane whereas the longer peduncles of plants of the male parent selection place the flowers above the foliar plane.

Plants of the new *Phlox* can also be compared to plants of *Phlox subulata* 'Crimson Beauty', not patented. In side-by-side comparisons, plants of the new *Phlox* and 'Crimson Beauty' differ in the following characteristics:

1. Plants of the new *Phlox* are more upright than and not as creeping as plants of 'Crimson Beauty'.
2. Plants of the new *Phlox* have larger flowers than plants of 'Crimson Beauty'.
3. Plants of the new *Phlox* and 'Crimson Beauty' differ in flower color as plants of the new *Phlox* have bright violet-colored flowers whereas plants of 'Crimson Beauty' have bright rosy red-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet (FIG. 1) comprises a side perspective view of typical flowering plant of 'Dophlowoblu' grown in a container.

Figure 2:
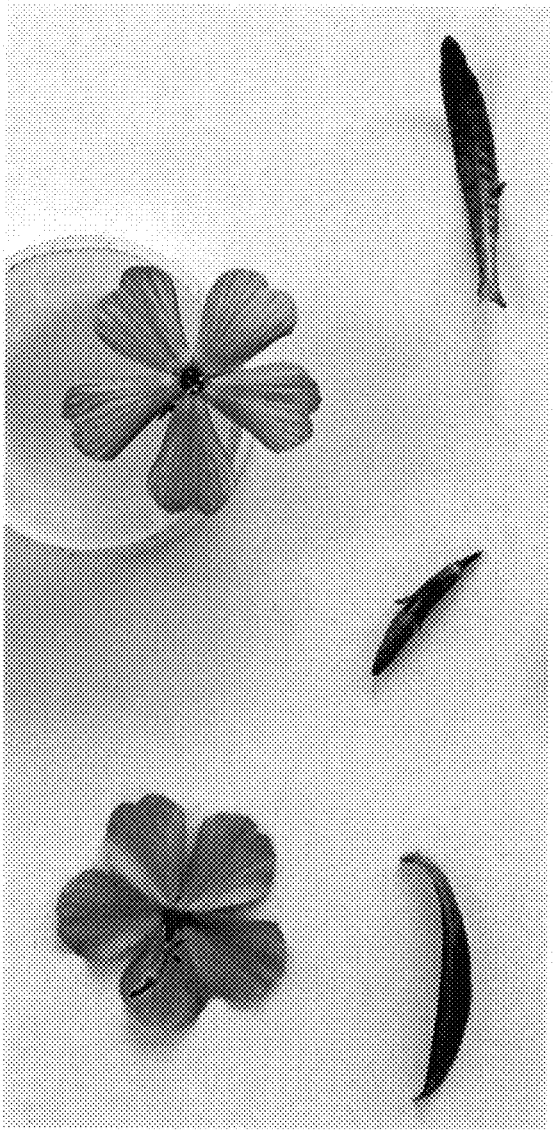

The photograph on the second sheet (FIG. 2) is a close-up view of the upper and lower surfaces of typical flowers and leaves and a typical flower bud of 'Dophlowoblu'.

DETAILED BOTANICAL DESCRIPTION

The aforementioned photographs and following observations, measurements and values describe plants grown during the spring in 13-cm containers in an outdoor nursery in Straelen, Germany under cultural practices typical of commercial *Phlox* production. During the production of the plants, day temperatures averaged 21 C and night temperatures averaged 15 C. Plants were pinched one time two weeks after planting rooted young plants and plants were 32 weeks old when the photographs and the description were taken. In the following description, color references are made to The Royal Horticultural Society Colour Chart, Fifth Edition, except where general terms of ordinary dictionary significance are used.

Botanical classification: *Phlox hybrida* 'Dophlowoblu'.

Parentage:

*Female, or seed, parent*.—Proprietary selection of *Phlox hybrida* identified as code number SB07-000252-016, not patented.

*Male, or pollen, parent*.—Proprietary selection of *Phlox hybrida* identified as code number SB-0064, not patented.

Propagation:

*Type*.—By vegetative cuttings.

*Time to initiate roots, summer*.—About 16 days at temperatures about 26 C.

*Time to initiate roots, winter*.—About three weeks at temperatures about 23 C.

*Time to produce a rooted young plant, summer*.—About 24 days at temperatures about 23 C.

*Time to produce a rooted young plant, winter*.—About four weeks at temperatures about 18 C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright to outwardly spreading and mounding plant habit; vigorous growth habit and moderate growth rate.

*Plant height*.—About 14 cm.

*Plant width* (*spread*).—About 25 cm.

*Lateral branches*.—Branching habit: Freely branching habit with about six primary lateral branches each with about eight secondary lateral branches developing per plant. Length: About 13 cm. Diameter: About 3 mm. Internode length: About 8 mm. Strength: Strong. Aspect: Erect to about 60 degrees from vertical. Texture and luster: Pubescent; glossy. Color: Close to 148A; with development, close to 148A tinged with close to N187A.

Leaf description:

*Arrangement*.—Opposite, decussate; simple; sessile.

*Length*.—About 3.5 cm.

*Width*.—About 5 mm.

*Shape*.—Lanceolate.

*Apex*.—Acuminate.

*Base*.—Cuneate.

*Margin*.—Entire, ciliate.

*Texture and luster, upper and lower surface*.—Smooth, glabrous; glossy.

*Venation pattern*.—Single midvein discernible.

*Color*.—Developing leaves, upper surface: Close to 146A. Developing leaves, lower surface: Close to 146C. Fully expanded leaves, upper surface: Close to NN137A; venation, close to NN137A. Fully expanded leaves, lower surface: Close to 137C; venation, close to 137C.

Flower description:

*Flower type and flowering habit*.—Single rotate and salverform flowers arranged in terminal and lateral panicles; flowers face mostly upright to outwardly depending on position on inflorescence; freely flowering habit with about twelve open flowers per inflorescence and about 195 flowers developing per plant during the flowering season.

*Fragrance*.—Faintly fragrant, pleasant.

*Natural flowering season*.—Plants begin flowering about 32 weeks after planting; plants flower for about three to four weeks in April and May in the garden in Germany; flowers persistent.

*Flower buds*.—Height: About 1.5 cm. Diameter: About 3 mm. Shape: Elliptic. Texture and luster: Smooth, glabrous; matte. Color: Close to 93C.

*Inflorescence height*.—About 9 cm.

*Inflorescence diameter*.—About 11 cm.

*Flower diameter*.—About 2.8 cm by 2.8 cm.

*Flower depth*.—About 1.8 cm.

*Flower throat diameter*.—About 3 mm.

*Flower tube length*.—About 9 mm.

*Flower diameter, proximally*.—About 2 mm.

*Petals*.—Quantity per flower: Typically five in a single whorl; petals fused at the base into a narrow tube.

Lobe length: About 1.5 cm. Lobe width: About 1.2 cm. Lobe shape: Obcordate. Lobe apex: Cordate. Lobe margin: Entire; not undulate. Lobe texture and luster, upper and lower surfaces: Smooth, glabrous; matte. Throat texture and luster: Smooth, glabrous; matte. Tube texture and luster: Pubescent; matte. Color: When opening, upper surface: Close to N87A. When opening, lower surface: Close to N88D. Fully opened, upper surface: Close to 92A; venation, close to 92A; color becoming closer to 91C to 91D with subsequent development. Fully opened, lower surface: Close to 92B; venation, close to 92B; color becoming closer to 91C with subsequent development. Throat: Close to 92A; venation, close to 92A. Tube: Close to 83A; venation, close to 83A.

*Sepals*.—Quantity per flower: Typically five in a single whorl, fused towards the base; calyx, tubular in shape. Length: About 9 mm. Width: About 2 mm. Shape: Narrowly deltoid, subulate. Apex: Acuminate. Margin: Entire. Texture and luster, upper surface: Pubescent; glossy. Texture and luster, lower surface: Glabrous; glossy. Color: When opening and fully opened, upper surface: Close to N137A. When opening and fully opened, lower surface: Close to N137A.

*Peduncles*.—Length: About 2.8 cm. Diameter: About 1 mm. Strength: Moderately strong. Aspect: Erect to about 65 degrees from lateral branch axis. Texture and luster: Pubescent; glossy. Color: Close to N137A tinged with close to 187A.

*Pedicels*.—Length: About 1.2 cm. Diameter: About 1 mm. Strength: Weak, flexible. Aspect: Erect to about 65 degrees from peduncle axis. Texture and luster: Pubescent; glossy. Color: Close to N137A tinged with close to 187A.

*Reproductive organs*.—Stamens: Quantity per flower: Typically five. Filament length: About 1 mm. Filament color: Close to 83A. Anther size: About 1 mm by 3 mm. Anther shape: Elliptic. Anther color: Close to 203D. Pollen amount: Abundant. Pollen color: Close to 21A. Pistils: Quantity per flower: One. Pistil length: About 1.7 cm. Stigma diameter: About 2 mm. Stigma shape: Cleft, three-parted. Stigma color: Close to NN144A. Style length: About 1.4 cm. Style color: Close to N87D. Ovary color: Close to 143A.

*Seeds and fruits*.—To date, seed and fruit development have not been observed on plants of the new *Phlox*.

Garden performance: Plants of the new *Phlox* have been observed to have good garden performance and to tolerate rain, wind, temperatures ranging from about −35 C to about 35 C and to be suitable for USDA Hardiness Zones 3 to 9.

Pathogen & pest resistance: To date, plants of the new *Phlox* have not been observed to be resistant to pathogens and pests common to *Phlox* plants.

It is claimed:

1. A new and distinct *Phlox* plant named 'Dophlowoblu' as illustrated and described.

* * * * *